US008440609B2

(12) United States Patent
Wallukat et al.

(10) Patent No.: US 8,440,609 B2
(45) Date of Patent: May 14, 2013

(54) PEPTIDES AGAINST AUTOANTIBODIES CAUSING INTOLERANCE TO COLD AND USE THEREOF

(76) Inventors: Gerd Wallukat, Berlin (DE); Thomas Harrer, Erlangen (DE)

( * ) Notice: Subject to any disclaimer, the term of this patent is extended or adjusted under 35 U.S.C. 154(b) by 1379 days.

(21) Appl. No.: 10/543,815

(22) PCT Filed: Jan. 29, 2004

(86) PCT No.: PCT/DE2004/000169
§ 371 (c)(1),
(2), (4) Date: Aug. 11, 2006

(87) PCT Pub. No.: WO2004/067549
PCT Pub. Date: Aug. 12, 2004

(65) Prior Publication Data
US 2007/0026396 A1    Feb. 1, 2007

(30) Foreign Application Priority Data

Jan. 31, 2003   (DE) .................................. 103 05 165
Mar. 6, 2003    (DE) .................................. 103 11 106

(51) Int. Cl.
*A61K 38/08*   (2006.01)
(52) U.S. Cl.
USPC ............................................. 514/1.1; 514/2.7
(58) Field of Classification Search ........................ None
See application file for complete search history.

(56) References Cited

U.S. PATENT DOCUMENTS

| 2001/0016350 A1 * | 8/2001 | Stutzman-Engwall et al. ................ 435/253.5 |
| 2003/0096390 A1 * | 5/2003 | Giver et al. .................. 435/198 |

FOREIGN PATENT DOCUMENTS

| JP | 2002 010784 | 1/2002 |
| WO | WO 00/66621 | * 11/2000 |
| WO | WO 01/35810 | * 5/2001 |

OTHER PUBLICATIONS

Wojtukiewicz et al., NCBI sequence viewer entry for Cancer Res, 1995 v55(3); 1 page.*
Wojtukiewicz et al, Cancer Research 1995 55:698-704.*
Namiki et al, JP 2002010784, 2002, abstract and structure entry from caplus 10 pages.*
Database EMBL Apr. 6, 1991 "Human Thrombin Receptor Mrna; Complete cds" XP002290141.

* cited by examiner

*Primary Examiner* — Cecilia J Tsang
*Assistant Examiner* — Ronald Niebauer
(74) *Attorney, Agent, or Firm* — Ursula B. Day

(57) ABSTRACT

The invention relates to nucleic acid molecules encoding peptides which are directed against autoantibodies associated with cold allergy, to the peptides themselves, to a pharmaceutical composition comprising said nucleic acid molecules and peptides, and to the use of said nucleic acid molecules and peptides for the treatment of circulatory disorders associated with exposure to cold or intolerance to cold, especially cold allergies.

3 Claims, No Drawings derlying cold allergy. The Raynaud syndrome alone occurs in 3 to 16% of the
population, with females being affected 5 to 10 times more
frequently than males. The first symptoms typically become
apparent at an age of from 14 to 40 years, with males being
affected at later stages of life. Inter alia, lack of an effective
therapy is inconvenient because merely putting one's hand in
a refrigerator or a freezer, touching a cold steering wheel or
washing one's hands with cold water is sufficient to induce
e.g. such a blood flow disturbance, especially the Raynaud
syndrome. In many such lives the acting persons are not
always able to avoid cold.

The Raynaud syndrome involves temporary interruption of
the blood supply in limbs, mostly fingers and toes, but some-
times ears and nose as well. During an attack, the limbs
initially turn white, generally being optically perceived as
lifeless already, subsequently blue and eventually red, accom-
panied by a burning sensation. The autoimmune reaction is
considerably painful, being accompanied by a numbness sen-
sation and itching. At present, offering affected persons an
effective and reliable diagnosis or therapy for such cold-
associated pathogenic changes is possible to only a very
limited extent. In general, the affected persons are advised to
avoid cold exposure of the extremities or warm up immedi-
ately in case vasospasms have already occurred. Furthermore,
some phenomenons of the disease can be treated by local
spraying of glycerol trinitrate. In some cases, success by
administration of calcium antagonists has also been reported.
The elimination of ganglions by sympathectomy has been
recommended as a last resort. As a result of such specific
dissection of nerves, the patient is temporarily free of discom-
fort, at least for some months or even years. More recently, the
Raynaud syndrome can be positively influenced by means of
a particular red-light laser. Disadvantageously, however, rou-
tine use of this new therapeutical method has not been pos-
sible for capacity reasons.

The object of the invention was therefore to provide com-
pounds allowing easy, reliable and effective diagnosis and
therapy of cold-associated circulatory disorders, particularly
Raynaud's syndrome.

The invention solves the above technical problem by pro-
viding an isolated nucleic acid molecule—and a peptide
encoded by same—selected from the group comprising:
a) a nucleic acid molecule comprising a nucleotide sequence
which encodes a peptide consisting of the following amino
acid sequences: ITTCHDVL (SEQ ID NO: 1), ITTCH-
DAL (SEQ ID NO: 2) or LNITTCHDV (SEQ ID NO: 3);
b) a nucleic acid molecule which is complementary to a
nucleotide sequence in accordance with a);
c) a nucleic acid molecule which undergoes hybridization
with a nucleotide sequence according to a) or b) under
stringent conditions;
d) a nucleic acid molecule comprising a nucleotide sequence
having sufficient homology to be functionally analogous to
a nucleotide sequence according to a), b) or c);
e) a nucleic acid molecule which, as a consequence of the
genetic code, is degenerated into a nucleotide sequence
according to a)-d), and
f) a nucleic acid molecule according to a nucleotide sequence
of a)-e) which is modified by deletions, additions, substi-
tutions, translocations, inversions and/or insertions and
functionally analogous to a nucleotide sequence according
to a)-e).

Accordingly, the invention involves the surprising teaching
that the nucleic acid molecules according to the invention, as
well as the peptides encoded by same, can be used for diag-
nosis and therapy in dysfunctions of heat regulation and circulatory disorders, especially in small blood vessels supplying particularly the hands, feet, ears, cheeks, nose and nipples with blood. More specifically, the biological structures, preferably peptides, encoded by said nucleic acid molecules can be used in various forms in the prophylaxis, diagnosis, therapy, follow-up and/or aftercare of circulatory disorders, especially cold allergy and more preferably the Raynaud syndrome.

In a preferred embodiment of the invention the nucleic acid molecule which has sufficient homology to be functionally analogous to the nucleic acid sequence in accordance with a), b) and/or c) has at least 40% homology. In the meaning of the invention the term "to be functionally analogous to the above-mentioned nucleotide sequences or to the sequences hybridizing with said nucleotide sequences" means that the homologues exhibit a behavior in circulatory disorders, especially cold allergy, such that reliable and effective use thereof is possible in diagnosis and/or therapy of such diseases or pathogenic conditions associated with said diseases. Functionally analogous sequences in the meaning of the invention are all those sequences which can be identified as equally effective by a person skilled in the art, using routine tests.

In another advantageous embodiment of the invention the nucleic acid molecule has at least 60%, preferably 70%, more preferably 80%, especially preferably 90% homology to the nucleic acid molecule in accordance with d).

In another preferred embodiment of the invention the nucleic acid molecule is a genomic DNA, a cDNA and/or an RNA.

The invention also relates to a vector comprising a nucleic acid molecule according to the invention and, in addition, to a host cell comprising said vector.

In a preferred fashion the invention also relates to a peptide encoded by a nucleic acid molecule according to the invention and by the preferred functionally analogous nucleic acid molecules. Surprisingly, the peptide according to the invention can be used in the diagnosis and/or therapy of diseases associated with intolerance to cold. More specifically, the peptides of the invention are bound by autoantibodies in patients suffering from acrocyanosis, cold hemagglutination disease, hyperviscosity syndrome, ischemia syndrome, acrotrophoneurosis, scleroderma, cold erythema, cold purpura, cold urticaria, cryopathy and/or cryoglobulinemia and, in particular, cold allergy and especially Raynaud's syndrome.

That is, the invention relates to all peptides encoded by the nucleic acid molecules according to the invention, preferably those having at least 60%, preferably 70%, more preferably 80%, especially preferably 90% homology to the nucleic acid molecule in accordance with d). Obviously, said functionally analogous nucleic acid molecules can be modified by deletion, addition, substitution, translocation, inversion and/or insertion in such a way that the peptides encoded by same interact with autoantibodies associated with the Raynaud syndrome. By virtue of the teaching according to the invention, a person skilled in the art will be capable of generating other equivalent peptides functionally analogous to peptides having the sequences ITTCHDVL (SEQ ID NO: 1), ITTCHDAL (SEQ ID NO: 2) or LNITTCHD (SEQ ID NO: 3) and LNITTCHDCL (SEQ ID NO: 4), respectively. Of course, it is also possible to use peptides comprising the above-mentioned structures, such as QTIQVPGLNITTCHDVLNETLL (SEQ ID NO: 5) or QTIFIPALNITTCHDVLPEQLL (SEQ ID NO: 6). Obviously, however, the peptides according to the invention would not be selected in a way so as to completely represent the naturally occurring PAR-1, -2 or -3 receptors. More specifically, the peptides according to the invention relate to selected regions of the second extracellular loop of the PAR-1, -2 or -3 receptors. However, the advantageous sequences ITTCHDVL (SEQ ID NO: 1), ITTCHDAL (SEQ ID NO: 2) or LNITTCHD (SEQ ID NO: 3) may also comprise further amino acids naturally flanking the above-mentioned sequences in the second extracellular loop of the receptor, in which case the size of the flanking regions should not be selected such that the receptors themselves would be selected. Examples of such sequences—expanded by flanking or other artificial regions—are LNITTCHDCL (SEQ ID NO: 4), QTIQVPGLNITTCHDVLNETLL (SEO ID NO: 5) or QTIFIPALNITTCHDVLPEQLL(SEO ID NO: 6).

Consequently, the peptides in the meaning of the invention can be designed in such a way and may include such a number of additional amino acids, spacers or other structures that they are suitable for interaction with the antibodies, and preferably in such a way that they represent an epitope for the latter.

Accordingly, the peptides according to the invention are not restricted to the sequences ITTCHDVL (SEQ ID NO: 1), ITTCHDAL (SEQ ID NO: 2) and/or LNITTCHD (SEQ ID NO: 3), but rather, the peptides are preferably antibody epitopes essentially including the above-mentioned or functionally analogous sequences, so that they represent and characterize the epitope in such a way that the antibodies would undergo specific interaction with them. Therefore, under particular conditions the terms "epitope" and "peptide" may also be used synonymously.

Furthermore, it is possible to replace single amino acids or groups of amino acids without adversely affecting the activity of the peptides with respect to accomplishing the object of the present invention. For replacement of such amino acids, reference is made to appropriate standard textbooks of biochemistry and genetics.

Various ways of preparing peptides have been disclosed in the prior art. Peptides designed starting from the peptides of the invention using such methods are included in the teaching according to the invention. For example, one way of generating functionally analogous peptides has been described in PNAS USA 1998, Oct. 13, 9521, 12179-84; WO 99/6293 and/or WO 02/38592; and the above teachings are hereby incorporated in the disclosure of the invention. That is, all peptides, peptide fragments or structures comprising peptides generated using the methods mentioned above—starting from the peptides of the invention—are peptides according to the invention, provided they accomplish the object of the invention and, in particular, interact with the pathogenic autoantibodies. For example, these autoantibodies can be agonistic autoantibodies activating receptors. Some preferred receptors will be described below.

For example, the peptide sequences can be a natural component of the second extracellular loop of the thrombin receptor (PAR-1), of the trypsin and tryptase receptor (PAR-2) and/or of the thrombin receptor or receptor of unknown proteases (PAR-3). Surprisingly, the autoantibodies specifically interact with the second extracellular loop or with the loop of the respective protease-activated receptor (PAR). Accordingly, the invention also relates to the surprising teaching that the major epitope of the autoantibodies associated with cold-induced diseases, especially cold allergy and especially preferably the Raynaud syndrome, are peptides having the amino acid sequence ITTCHDVL (SEQ ID NO: 1), ITTCHDAL (SEQ ID NO: 2) and/or LNITTCHD (SEQ ID NO: 3). Preferably, this sequence is entirely identical on PAR-1 and PAR-2. In PAR-3, the valine (V) situated near the C-terminal end is replaced by alanine (A). Accordingly, the autoantibodies can be antibodies acting as agonistic autoantibodies, i.e., these autoantibodies are capable of activating the corresponding receptors by binding thereto. As a result of such receptor activation, various diseases or pathogenic changes can be induced and/or accompanied. For example, it is possible that activation of receptors modulates the production of messenger molecules. However, the autoantibodies may also damage receptors of cells which are responsible for essentially normal blood flow in limbs. In contrast to the effect of agonistic autoantibodies, the function of attacking and damaging the corresponding target by chronic stressing—usually observed with antibodies—is the predominant one in non-agonistic autoantibodies. However, this does not exclude activation or deactivation of the receptors.

In a preferred embodiment of the invention the peptide additionally comprises amino groups, amides, acetyl groups, biotin groups, markers, spacers and/or linkers.

By virtue of such structures, the peptide can be used with advantage in various fields of diagnosis and therapy of autoimmune diseases. Various ways of modifying peptides for various applications are well-known to those skilled in the art. If, for example, the peptides are envisaged to be administered as a drug, e.g. on the oral route, the structure of the peptides has to be changed in an specific fashion, as is well-known to those skilled in the art. However, the peptides may also be bound to the supporting material of an affinity column in order to be used in the purification of body fluids, especially blood; binding of the peptides to a matrix requires specific structural modifications of the peptides according to the invention, and such modifications are also well-known to those skilled in the art or can be determined using routine tests.

In another preferred embodiment the peptide has the amino acid sequence X1-X2-X3-X4-X5-X6-X7-X8-X9-X10 wherein X1=amino group, amide, acetyl group, biotin group, marker, spacer, linker, GKK, SGKK (SEQ ID NO: 7) or deletion,
X2=I, L, V, A,
X3=T, N, D, R,
X4=T, I, L, A,
X5=C, T, A, S,
X6=H, T, S, A,
X7=D, C, G, E,
X8=V, H, A, L,
X9=L, D, Y, F,
X10=amino group, amide, acetyl group, biotin group, marker, spacer, linker, GKK, SGKK (SEQ ID NO: 7) or deletion.

As is well-known to those skilled in the art, some amino acids have analogous physicochemical properties so that these amino acids advantageously can be replaced by each other. For example, these include the group of amino acids (a) glycine, alanine, valine, leucine and/or isoleucine; or the amino acids (b) serine and threonine, the amino acids (c) asparagine and glutamine, the amino acids (d) aspartic acid and glutamic acid; the amino acids (e) lysine and arginine, as well as the group of aromatic amino acids (f) phenylalanine, tyrosine and/or tryptophan. Amino acids within one and the same group (a-f) can be replaced with one another. Furthermore, the amino acids can be replaced by modified amino acids or specific enantiomers. Further modifications are possible in accordance with the teaching of WO 99/62933 or WO 02/38592.

In another preferred embodiment the peptide comprises a linker and/or a spacer selected from the group comprising α-aminocarboxylic acids as well as homo- and heterooligomers thereof, α,ω-aminocarboxylic acids and branched homo- or heterooligomers thereof, other amino acids, as well as linear and branched homo- or heterooligomers (peptides); amino-oligoalkoxyalkylamines; maleinimidocarboxylic acid derivatives; oligomers of alkylamines; 4-alkylphenyl derivatives; 4-oligoalkoxyphenyl or 4-oligoalkoxyphenoxy derivatives; 4-oligoalkylmercaptophenyl or 4-oligoalkylmercaptophenoxy derivatives; 4-oligoalkylaminophenyl or 4-oligoalkylaminophenoxy derivatives; (oligoalkylbenzyl)phenyl or 4-(oligoalkylbenzyl)phenoxy derivatives, as well as 4-(oligoalkoxybenzyl)phenyl or 4-(oligoalkoxybenzyl)phenoxy derivatives; trityl derivatives; benzyloxyaryl or benzyloxyalkyl derivatives; xanthen-3-yloxyalkyl derivatives; (4-alkylphenyl)- or ω-(4-alkylphenoxy)alkanoic acid derivatives; oligoalkylphenoxyalkyl or oligoalkoxyphenoxyalkyl derivatives; carbamate derivatives; amines; trialkylsilyl or dialkylalkoxysilyl derivatives; alkyl or aryl derivatives and/or combinations thereof; other possible structures have been described in EP 1 214 350 which hereby is incorporated in the disclosure of the invention.

According to another particularly preferred embodiment of the invention, the peptide is selected from the group comprising:
a) a peptide comprising the amino acid sequence ITTCHDVL (SEQ ID NO: 1), ITTCHDAL (SEQ ID NO: 2) and/or LNITTCHD (SEQ ID NO: 3);
b) a peptide comprising an amino acid sequence having sufficient homology to be functionally analogous to an amino acid sequence in accordance with a);
c) a peptide according to an amino acid sequence a) or b) which is modified by deletions, additions, substitutions, translocations, inversions and/or insertions and functionally analogous to an amino acid sequence in accordance with a) or b).

In a distinctive embodiment of the invention the peptide which has sufficient homology to be functionally analogous to one of the following amino acids ITTCHDVL (SEQ ID NO: 1), ITTCHDAL (SEQ ID NO: 2) and/or LNITTCHD (SEQ ID NO: 3) has at least 40% homology thereto.

In another preferred embodiment said amino acid sequences have at least 60%, preferably 70%, more preferably 80%, especially preferably 90% homology to one of the following amino acid sequences: ITTCHDVL (SEQ ID NO: 1), ITTCHDAL (SEQ ID NO: 2) and/or LNITTCHD (SEQ ID NO: 3).

In an especially preferred embodiment of the invention the peptide essentially consists of the amino acid sequence ITTCHDVL (SEQ ID NO: 1), ITTCHDAL (SEQ ID NO: 2) and/or LNITTCHD (SEQ ID NO: 3) More specifically, the peptide consists of modifications of said sequences, which are obtained according to WO 99/62933 and WO 02/38592, and it goes without saying that these peptides bind autoantibodies in the meaning of the invention.

In another preferred embodiment of the invention the peptide is used or employed as a therapeutic active substance. In the meaning of the invention, use as a therapeutic active substance means use of the peptide in the entire field of medicine.

In another particularly preferred embodiment of the invention the peptide is bound by specific antibodies of patients with cold allergy, especially by autoantibodies. At a defined quantity ratio of peptide and autoantibody, which is well-known to those skilled in the art, autoantibody-peptide complexes will form which, for example, undergo precipitation or exhibit specific reaction behavior in a way so as to allow elimination of the autoantibodies.

In another preferred embodiment of the invention the peptide, in particular, is immobilized. In the meaning of the invention, immobilization is understood to involve various methods and techniques to fix the peptides on specific carriers, e.g. according to WO 99/56126 or WO 02/26292. For example, immobilization can serve to stabilize the peptides so that their activity would not be reduced or adversely modified by biological, chemical or physical exposure, especially during storage or in single-batch use. Immobilization of the peptides allows repeated use under technical or clinical routine conditions; furthermore, a sample—preferably blood components—can be reacted with at least one of the peptides according to the invention in a continuous fashion. In particular, this can be achieved by means of various immobilization techniques, with binding of the peptides to other peptides or molecules or to a carrier proceeding in such a way that the three-dimensional structure—particularly in the active center mediating the interaction with the autoantibodies—of the corresponding molecules, especially of said peptides, would not be changed. Advantageously, there is no loss in specificity to the autoantibodies of the patient as a result of such immobilization. In the meaning of the invention, three basic methods can be used for immobilization:

(i) Crosslinking: in crosslinking, the peptides are fixed to one another without adversely affecting their activity. Advantageously, they are no longer soluble as a result of such crosslinking.
(ii) Binding to a carrier: binding to a carrier proceeds via adsorption, ionic binding or covalent binding, for example. Such binding may also take place inside microbial cells or liposomes or other membranous, closed or open structures. Advantageously, the peptides are not adversely affected by such fixing. For example, multiple or continuous use of carrier-bound peptides is possible with advantage in clinics in diagnosis or therapy.
(iii) Inclusion: inclusion in the meaning of the invention especially is inclusion in a semipermeable membrane in the form of gels, fibrils or fibers. Advantageously, encapsulated peptides are separated from the surrounding sample solution by a semipermeable membrane in such a way that interaction with the autoantibodies or fragments thereof still is possible.

Various methods are available for immobilization, such as adsorption on an inert or electrically charged inorganic or organic carrier. For example, such carriers can be porous gels, aluminum oxide, bentonite, agarose, starch, nylon or polyacrylamide. Immobilization proceeds via physical binding forces, frequently involving hydrophobic interactions and ionic binding. Advantageously, such methods are easy to handle, having little influence on the conformation of the peptides. Advantageously, binding can be improved as a result of electrostatic binding forces between the charged groups of the peptides and the carrier, e.g. by using ion exchangers such as Sephadex.

Another method is covalent binding to carrier materials. In addition, the carriers may have reactive groups forming homopolar bonds with amino acid side chains. Suitable groups in peptides are carboxy, hydroxy and sulfide groups and especially the terminal amino groups of lysines. Aromatic groups offer the possibility of diazo coupling. The surface of microscopic porous glass particles can be activated by treatment with silanes and subsequently coated with peptides. For example, hydroxy groups of natural polymers can be activated with bromocyanogen and subsequently coupled with peptides. Advantageously, a large number of peptides can undergo direct covalent binding with polyacrylamide resins. Inclusion in three-dimensional networks involves inclusion of the peptides in ionotropic gels or other structures well-known to those skilled in the art. More specifically, the pores of the matrix are such in nature that the peptides are retained, allowing interaction with the target molecules. In crosslinking, the peptides are converted into polymer aggregates by crosslinking with bifunctional agents. Such structures are gelatinous, easily deformable and, in particular, suitable for use in various reactors. By adding other inactive components such as gelatin in crosslinking, advantageous improvement of mechanical and binding properties is possible. In microencapsulation, the reaction volume of the peptides is restricted by means of membranes. For example, microencapsulation can be carried out in the form of an interfacial polymerization. Owing to the immobilization during microencapsulation, the peptides are made insoluble and thus reusable. In the meaning of the invention, immobilized peptides are all those peptides being in a condition that allows reuse thereof. Restricting the mobility and solubility of the peptides by chemical, biological or physical means advantageously results in lower process cost, particularly when eliminating autoantibodies from blood components.

In another preferred embodiment of the invention the peptide is bound to a solid phase. Binding the peptide to the solid phase may proceed via a spacer. All those chemical compounds can be used as spacers which have the structural and functional preconditions suitable for the function of a spacer, provided they do not modify the binding behavior in such a way that binding of the autoantibody with the peptide would be adversely affected.

The invention also relates to recognition molecules directed against the nucleic acid molecules of the invention, the vectors of the invention, the host cells of the invention and/or against the peptides according to the invention. In a preferred fashion the recognition molecules are antibodies, antisense constructs and/or chelating agents. The recognition molecules according to the invention can be antibodies directed against the autoantibodies inducing e.g. a cold allergy, especially the Raynaud syndrome.

The invention also relates to a pharmaceutical composition comprising the inventive nucleic acid molecules, vectors, host cells, peptides and/or recognition molecules, optionally together with a pharmaceutically tolerable carrier. In particular, the pharmaceutical composition can be used as a drug. To this end, it is possible, for example, to modify the peptides by means of cyclization or other procedures well-known to those skilled in the art such that destruction thereof by endogenous peptide-degrading structures, e.g. serum proteases, is prevented. By using the peptides or recognition molecules according to the invention, in vivo or ex vivo neutralization of autoantibodies is possible. In in vivo neutralization, the drugs are administered directly to the patient; in ex vivo neutralization, the blood is conducted out of the body e.g. via a loop, e.g. in the form of a tube circulation, subsequently contacted with the drug and, following neutralization of the autoantibodies, resupplied into the organism, i.e., the patient. Regarded as drugs in the meaning of the invention are compositions for therapeutic and prophylactic purposes, as well as pharmaceutical compositions usable as diagnostic agents. According to the invention, drugs or pharmaceutical compositions—used in a synonymous fashion herein—are substances and formulations of substances intended to cure, alleviate or avoid diseases, illness, physical defects or pathological affection by application on or in the human body. According to the invention, medical adjuvants are substances used as active ingredients in the production of drugs. Pharmaceutical-technical adjuvants serve to suitably formulate the drug or pharmaceutical composition and, if required during the production process only, can even be removed thereafter, or they can be part of the pharmaceutical composition as pharmaceutically tolerable carriers. Examples of pharmaceutically tolerable carriers will be given below. Drug formulation or formulation of the pharmaceutical composition is optionally effected in combination with a pharmaceutically tolerable carrier and/or diluent. Examples of suitable pharmaceutically tolerable carriers are well-known to those skilled in the art and comprise e.g. phosphate-buffered saline, water, emulsions such as oil/water emulsions, various types of detergents, sterile solutions, and so forth. Drugs or pharmaceutical compositions comprising such carriers can be formulated by means of well-known conventional methods. These drugs or pharmaceutical compositions can be administered to an individual at a suitable dose, e.g. in a range of from 1 µg to 10 g of peptides per day and patient. Doses of from 1 mg to 1 g are preferred. Preferred is administration of doses as small in number and as low as possible, preferably a single dose. Administration can be effected on various routes, e.g. intravenous, intraperitoneal, intrarectal, intragastrointestinal, intranodal, intramuscular, local, e.g. intratumoral, but also subcutaneous, intradermal or on the skin or via mucosa. Administration of nucleic acids encoding the peptide according to the invention can also be effected in the form of a gene therapy, e.g. via viral vectors. The kind of dosage and route of administration can be determined by the attending physician according to clinical factors. As is familiar to those skilled in the art, the kind of dosage will depend on various factors such as size, body surface, age, sex, or general health condition of the patient, but also on the particular agent being administered, the time period and type of administration, and on other medications possibly administered in parallel. Those skilled in the art will also be familiar with the fact that the concentration of autoantibodies can be diagnosed first, using the peptides according to the invention, in order to determine the required concentration of drug.

More specifically, the pharmaceutical compositions or drugs comprise a pharmacological substance which includes one or more peptides or recognition molecules of the invention, or/and nucleic acid molecules encoding same, in a suitable solution or administration form. Administration thereof can be effected either alone or together with appropriate adjuvants described in connection with drugs or pharmaceutical compositions, or in combination with one or more adjuvants, e.g. QS-21, GPI-0100 or other saponines, water-oil emulsions such as Montanide adjuvants, polylysine, polyarginine compounds, DNA compounds such as CpG, Detox, bacterial vaccines such as typhoid vaccines or BCG vaccines, salts such as calcium phosphates, and/or other suitable material enhancing the effect, preferably immunostimulatory molecules such as interleukins, e.g. IL-2, IL-12, IL-4 and/or growth factors such as GM-CSF. They are mixed with the peptides or recognition molecules of the invention according to well-known methods and administered in suitable formulations and dosages. Formulations, dosages and suitable components are well-known to those skilled in the art.

Obviously, the pharmaceutical composition or drug can also be a combination of two or more of the inventive pharmaceutical compositions or drugs, as well as a combination with other drugs, such as antibody therapies, chemotherapies or radiotherapies, suitably administered or applied at the same time or separately in time. The production of the drugs or pharmaceutical compositions proceeds according to per se known methods.

The invention also relates to a kit comprising the nucleic acid molecule, the vector, the host cell, the peptide and/or the recognition molecule, optionally together with instructions or information as to the pharmaceutical provision or the procedure of therapeutical treatment. For example, the information can be an instruction leaflet or other medium providing the user with information in which therapeutical procedure the above-mentioned substances should be used. In particular, the instruction leaflet includes detailed and/or important information about the therapeutical treatment. Obviously, the information need not necessarily be in the form of an instruction leaflet, and the information may also be imparted via the Internet.

The invention also relates to an apparatus for chromatography, which includes the peptides according to the invention.

In a preferred embodiment the peptides are bound to a solid phase within the chromatography system.

In particular, the apparatus according to the invention can be used to eliminate the autoantibodies from fluids of a patient or to neutralize the autoantibodies. This method is known to those skilled in the art under the term of immunoadsorption and apheresis therapy. With the aid of immunoadsorption, immunoglobulins are removed from the blood of a patient. Advantageously, this immunoadsorption treatment can be conducted in a stationary and ambulant fashion. It can be envisaged that the apparatus, particularly the so-called adsorber, is part of an extracorporeal blood circulation. To this end, blood is taken continuously or discontinuously from a patient's major vessel, particularly from an arm vein, and separated into single components, such as cellular and humoral components, using filtration or centrifugation. In particular, one essential blood component obtained in this fashion is blood plasma. Advantageously, the blood plasma can be passed through the apparatus of the invention and, following adsorption of the autoantibodies, returned into the patient, particularly through another vein of arms or legs, together with previously separated blood components, especially cellular components. It can also be envisaged that the peptides are immobilized on a Sepharose matrix. The matrix can be placed in a container having a volume of 10 to 400 ml. Thereafter, the blood plasma of the patient can be passed over the matrix where the autoantibodies will be bound, thus allowing elimination thereof from the blood plasma. Those skilled in the art will be familiar with various ways of providing such solid phase-fixed peptides, e.g. in the form of (i) regeneratable adsorption columns, (ii) double columns and (iii) disposable columns. The diverse wash and elution solutions, permitting high efficiency of treatment, can easily be determined by a person skilled in the art by using routine tests. By providing the teaching according to the invention, particularly the peptides of the invention, various ways of employing the peptides in vivo, ex vivo and in vitro in prophylaxis, diagnosis, therapy and aftercare of cold-induced, autoantibody-mediated diseases are disclosed to a person skilled in the art.

The invention also relates to a method for the treatment of cold allergy by binding and/or removing autoantibodies by means of peptides of the invention bound to a solid phase.

In a preferred embodiment of the invention the autoantibodies are directed against PAR-1, PAR-2 and/or PAR-3.

The invention also relates to the use of the nucleic acid molecules of the invention, the host cells of the invention, the vector of the invention, the peptides of the invention, the recognition molecules of the invention, the pharmaceutical composition of the invention, the kit of the invention and the apparatus of the invention in the prophylaxis, diagnosis, therapy, follow-up and/or aftercare of circulatory disorders.

The invention also relates to the use of the nucleic acid molecules of the invention, the host cells of the invention, the vector of the invention, the peptides of the invention, the recognition molecules of the invention, the pharmaceutical composition of the invention, the kit of the invention and the apparatus of the invention in the production of a drug for the treatment of circulatory disorders.

In a preferred embodiment of the invention the circulatory disorders are acrocyanosis, cold hemagglutination disease, hyperviscosity syndrome, ischemia syndrome, acrotrophoneurosis, scleroderma, cold erythema, cold purpura, cold urticaria, cryopathy and/or cryoglobulinemia. Acrocyanosis in the meaning of the invention is any discoloration of the acra during general cyanosis due to local, venous-capillary vasomotoric disorders occurring to a greater extent in cold and wet weather and involving a tendency of cold injuries. According to the invention, acrocyanosis particularly is A. anaesthetica, A. frigore and/or A. juvenile. Cold hemagglutination disease in the meaning of the invention is an acquired disease based on the formation of cold hemagglutinins. It may result in hemolysis, for example, particularly in those cases where the ambient temperature falls below 20° C. According to the invention, hyperviscosity syndrome is a disease wherein the blood flowability is reduced by an increased viscosity. In the meaning of the invention, the ischemia syndrome is classified into the acral and intermittent ischemia syndromes. In the meaning of the invention, these are understood to be any functional, organic and mixed functional organic circulatory disorders in hands and feet. In a stricter sense, this may also be the Raynaud syndrome, for example. Acrotrophoneurosis represents a disturbance in histotrophic blood flow in limbs, especially in the limb ends. Scleroderma in the meaning of the invention is a generic term for diseases with a chronic course, involving connective tissue sclerotization of localized skin areas or general affliction of the skin, involving internal organs. In the meaning of the invention, scleroderma is classified into a diffuse or progressive and circumscribed scleroderma. Cold erythema, for example, is an acute tissue lesion as a result of exposure to cold, particularly as a result of inadequate circulation, but also as a result of direct thermal attack. For example, it may give rise to discontinuous nerve degeneration, muscle and fat tissue necroses, as well as bone damage. Cold purpura in the meaning of the invention is a slight hemorrhage in the area of the hair follicles as a result of exposure to cold. Cold urticaria is understood to be formation of wheals following contact of an area of the skin with a cold object, cold water or cold wind. Cryopathy in the meaning of the invention is a local disease or a general state of disease following true cold lesion, or a disease involving the appearance of cold globulins in constitutional intolerance to cold.

According to another preferred embodiment of the invention the circulatory disorder is a cold allergy.

In a particularly preferred fashion the cold allergy is a Raynaud syndrome. According to the invention, a classification into primary and secondary Raynaud syndrome is made. Primarily, the disease is a functional disorder of the small supplying vessels of the acra, with no recognizable basic disease. For example, one characteristic is bilateral affliction, also referred to as symmetry, of hands or toes. The inconveniences of the primary disease subside with age. This disease occurs in 20% of the Raynaud patients. The secondary disease frequently is an asymmetric affliction of both hands or feet, reflecting another basic disease such as nerve lesions with particular medications such as migraine remedies. Frequently, the disease is associated with an organic vascular disease, especially a vascular inflammation in the course of a connective tissue disease, a so-called collagenosis. As the disease progresses, growth disorders of the nails and necrosis of the finger tips (sclerotizing phenomenon) may occur.

The invention also relates to the use of the inventive peptides and nucleic acids or host cells, the pharmaceutical composition of the invention, the kit of the invention and/or the apparatus of the invention in drug screening. For example, drug screening may comprise the identification of substances, particularly peptides, proteins, carbohydrates and/or lipids, which interact with the peptides and, accordingly, with the loops, particularly the second loop of PAR-1, PAR-2 and/or PAR-3.

Interaction, for example, can be binding to said peptides, but also activation or inhibition of or by peptides. Accordingly, a drug can be e.g. a structure binding to the peptides in the body of a patient, and consequently to the loops, thus competing with the autoantibodies for a binding site. By virtue of the disclosure of the teaching according to the invention, especially the disclosure with respect to the connection of disease and binding site of the autoantibodies, a person skilled in the art will be capable of screening various drugs. Drug screening based on disclosed targets is part of the general knowledge of a person skilled in the art and is effected using routine tests; reference is made to the corresponding standard textbooks of molecular biology and pharmacology.

The invention also relates to a method for the treatment of an autoimmune disease by binding and/or removal of autoantibodies by means of the inventive peptides bound to a solid phase. The autoantibodies are bound, complexed and/or neutralized on the solid phase by means of the peptides bound to the solid phase.

In a preferred embodiment of the invention, autoantibodies directed against PAR-1, PAR-2 and/or PAR-3 are bound, complexed and/or neutralized by means of the above-mentioned inventive materials and products, apparatus, particularly the chromatography apparatus, and peptides. For example, the peptides can be used in the detection of autoantibodies in serums of patients, using an ELISA or other immunological detection methods well-known to those skilled in the art. For detection, it can be advantageous, for example, when the autoantibodies are bound by biotinylated or otherwise coupled peptides and separated by streptavidin-coupled supports such as magnetic particles or plates. Such a method has been described in DE 102 56 897.9 which hereby is incorporated in the disclosure of the present application. More specifically, the separated autoantibodies are detected using igG subtype-specific labelled antibodies. In the event of a Raynaud syndrome, the antibodies are detected using particularly $igG_1$ subtype-specific labelled antibodies.

Without intending to be limiting, the invention will be explained in more detail with reference to the examples.

EXAMPLES

I. Affinity-Chromatographic Purification of the Antibodies

The biotinylated peptide sequence LNITTCHD (SEQ ID NO: 3) or LNITTCHDCL (SEQ ID, NO: 4) of the second extracellular loop of the PAR-2 receptor is used for affinity-chromatographic purification of autoantibodies against the PAR-2 receptor. As the above-mentioned sequence has been identified as epitope of the autoantibodies on the second extracellular loop of the PAR-2 and PAR-1 receptors, this sequence allows purification of autoantibodies against the PAR-1, PAR-2 receptors and of those against the PAR-3 receptor.

Using ammonium sulfate precipitation and subsequent dialysis, the immunoglobulin fractions are obtained from patient serums. The IgG fractions (1 ml) are mixed with 300 μl of peptide solution (100 μg/ml) and incubated for 1 hour at room temperature. The mixture containing the antibody-peptide complex is added to the streptavidin-magnetic particles previously washed 3 times with phosphate-buffered physiological saline (PBS, pH 7.2). After one hour the particles are separated in a magnetic field, washed 3 times with PBS and, subsequent to the last separation, the antibodies are eluted from the magnetic particles using 300 µl of 3 M KSCN solution. Subsequently, the eluates are dialyzed against the PBS solution. Thereafter, the purified PAR receptor autoantibodies and the immunoglobulin fractions from which the antibodies were removed are assayed for their functional activity in a bioassay (spontaneously pulsating rat cardiac myocytes).

II. Neutralization of Agonistic PAR Receptor Autoantibodies

To neutralize the functional autoantibodies, synthesized peptides corresponding to the second extracellular loop of the PAR-1 (QTIQVPGLNITTCHDVLNETLL) (SEQ ID NO: 5) or PAR-2 (QTIFIPALNITTCHDVLPEQLL) (SEQ ID NO: 6) receptor are incubated with the immunoglobulin fractions prepared from serums of patients suffering from Raynaud's syndrome.

Similarly, incubation is performed with the amino acid sequence LINTTCHDVL (SEQ ID NO: 8) of the extracellular loop of the PAR-1 and PAR-2 receptors, which has been identified as antibody epitope. The immunoglobulin fractions (50 µl) are incubated with 50 µl of peptide solution (10 µg/ml) for 1 hour at room temperature. The peptide-antibody complex is subsequently investigated in a bioassay with respect to its functional activity. Following pretreatment of the antibodies with the appropriate peptide, the agonistic effect was gone. Peptides corresponding to the first extracellular loop of the PAR receptor or to the second extracellular loop of the β1-adrenergic receptor or of the angiotensin II AT1 receptor failed to exhibit a neutralizing effect to PAR receptors.

We claim:

1. An isolated peptide, which is:

a peptide consisting of the amino acid sequence SEQ ID NO:3 and is capable of binding to PAR autoantibodies.

2. A medically active substance which comprises the peptide according to claim 1 and a carrier.

3. A pharmaceutical composition comprising the polypeptide according to claim 1 and a pharmaceutically tolerable carrier.

* * * * *

```
                        SEQUENCE LISTING

<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Thr Thr Cys His Asp Val Leu
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Thr Thr Cys His Asp Ala Leu
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Asn Ile Thr Thr Cys His Asp
 1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Asn Ile Thr Thr Cys His Asp Cys Leu
 1               5                  10
```

```
<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Thr Ile Gln Val Pro Gly Leu Asn Ile Thr Thr Cys His Asp Val
  1               5                  10                  15

Leu Asn Glu Thr Leu Leu
             20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Thr Ile Phe Ile Pro Ala Leu Asn Ile Thr Thr Cys His Asp Val
  1               5                  10                  15

Leu Pro Glu Gln Leu Leu
             20

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Gly Lys Lys
  1

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ile Asn Thr Thr Cys His Asp Val Leu
  1               5                  10
```